United States Patent

Niederhauser et al.

[11] Patent Number: 5,295,961
[45] Date of Patent: Mar. 22, 1994

[54] CATHETER SYSTEM FOR MECHANICAL DILATATION OF CORONARY STENOSES

[75] Inventors: Werner Niederhauser; Eugen Hofmann, both of Zurich; Susanne Pfenninger-Ganz, Uster, all of Switzerland

[73] Assignee: Schneider (Europe) A.G., Bulach, Switzerland

[21] Appl. No.: 904,231

[22] Filed: Jun. 25, 1992

[51] Int. Cl.⁵ .......................................... A61M 29/02
[52] U.S. Cl. ........................................ 604/96; 606/194
[58] Field of Search ................... 606/191, 194, 195; 604/95–102, 160

[56] References Cited

U.S. PATENT DOCUMENTS

| | | | |
|---|---|---|---|
| 4,544,745 | 7/1990 | Sogard et al. | 604/96 |
| 4,581,017 | 4/1986 | Sahota . | |
| 4,661,094 | 4/1987 | Simpson . | |
| 4,782,834 | 11/1988 | Maguire et al. . | |
| 4,877,031 | 10/1989 | Conway et al. | 604/96 |
| 4,892,519 | 1/1990 | Songer et al. | 604/96 |
| 4,988,356 | 1/1991 | Crittenden et al. | 604/96 |
| 5,090,958 | 2/1992 | Sahota | 604/98 |
| 5,135,535 | 8/1992 | Kramer . | |
| 5,154,725 | 10/1992 | Leopold | 604/102 |

FOREIGN PATENT DOCUMENTS

| | | |
|---|---|---|
| 441384 | 8/1991 | European Pat. Off. . |
| 0464714 | 1/1992 | European Pat. Off. ............ 604/102 |
| 9106499 | 9/1991 | Fed. Rep. of Germany . |
| WO92/17236 | 10/1992 | PCT Int'l Appl. . |
| WO92/20397 | 11/1992 | PCT Int'l Appl. . |

Primary Examiner—Stephen C. Pellegrino
Assistant Examiner—William W. Lewis
Attorney, Agent, or Firm—Peter C. Richardson; Lawrence C. Akers; Eric M. Lee

[57] ABSTRACT

A catheter system for mechanical dilatation of coronary arterial stenoses includes a balloon dilatation catheter, a guide wire and a guide catheter. The balloon dilatation catheter has, for the perfusion of vessel fluid during dilatation, side openings arranged both distal and proximal of the balloon and connected to one another via a lumen extending within the balloon. The internal lumen configuration of the balloon dilatation catheter permits the catheter system to be utilized as either a "monorail"-type or an "over-the-wire" system.

16 Claims, 5 Drawing Sheets

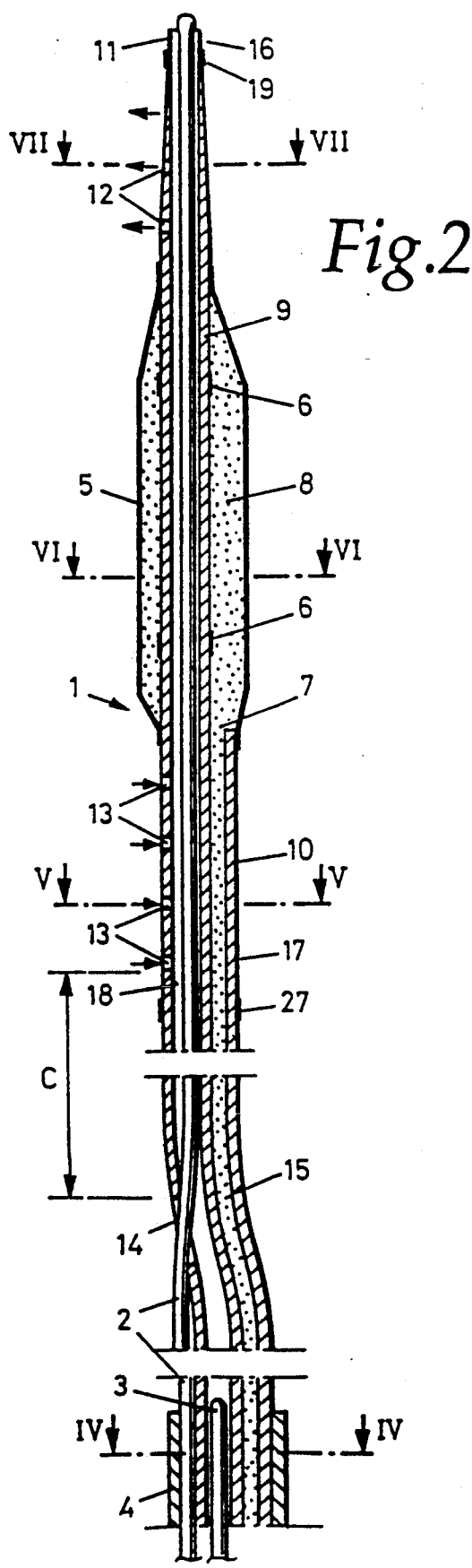
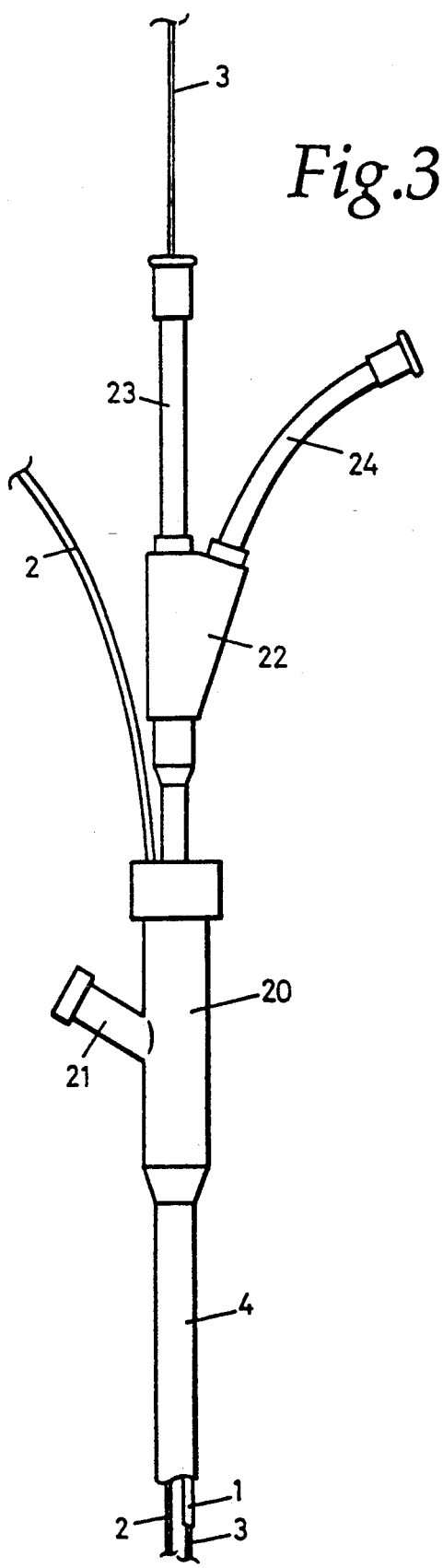

CATHETER SYSTEM FOR MECHANICAL DILATATION OF CORONARY STENOSES

BACKGROUND OF THE INVENTION

The invention relates to a catheter system for mechanical dilatation of coronary arterial stenoses, with a balloon dilatation catheter, a guide wire and a guide catheter, the balloon dilatation catheter having, for the perfusion of vessel fluid during dilatation, side openings arranged distal and proximal of the balloon and connected to one another via a lumen extending within the balloon.

Percutaneous dilatation of coronary stenoses using a balloon dilatation catheter was introduced in 1976 by A. Grüntzig and has proven to be a very effective and well-tolerated procedure. In order to lengthen the dilatation time without increased risk of ischaemia, and thereby to reduce the risk of restenosis, a balloon dilatation catheter is known having side openings connected to one another upstream and downstream of the balloon for the perfusion of vessel fluid. In this way, a blood flow corresponding to the natural pressure gradient is maintained even during balloon dilatation In this known catheter, there is the difficulty that the side openings are often blocked partially or completely by the blood plasma after a certain time, as a result of which the desired blood flow is reduced. In the event of a considerable blockage of the side openings, the balloon catheter must be replaced. The aim of the present invention is to provide a catheter system which avoids the stated difficulty.

SUMMARY OF THE INVENTION

In the catheter system according to the invention, the shaft of the balloon dilatation catheter is designed with two lumina, the second lumen being used for dilatation and filling of the balloon.

By way of the first lumen, the side openings of the balloon dilatation catheter which are intended for the perfusion can be flushed via a so-called Y-connector with a suitable fluid, for example a heparin solution. The important point is that the first lumen leading outwards at both ends of the catheter is suitable for receiving a temporary strengthening wire as well as for receiving a guide wire, and a flushing solution can be conveyed to the side openings via this lumen too.

Another important feature is that the catheter arrangement according to the invention can be used both as a "monorail"-type catheter (U.S. Pat. No. 4,762,129) and as an "over-the-wire catheter". This permits the following advantageous treatment method. The stenosis is first treated using a catheter arrangement according to the monorail system. After this first treatment, the balloon dilatation catheter is removed, the guide wire remaining in position. The balloon dilatation catheter of the arrangement according to the invention is then introduced over this indwelling guide wire, this guide wire, as in the monorail system, pressing into the catheter and leaving the catheter upstream and downstream of the balloon through the lateral outlet opening and the end hole, respectively. In this case, if necessary, the strengthening wire can be introduced into the first lumen of the balloon dilatation catheter. In order to ensure an adequate flow of vessel fluid right through the balloon segment upon dilatation of the stenosis, the guide wire is pulled back up to in front of what is the last side opening in the proximal direction. This position can be established by means of a gold marking which is visible by X-ray. If, despite the marking, the controllable guide wire is inadvertently withdrawn completely from the outlet opening, the lateral outlet opening of the indwelling balloon dilatation catheter can no longer be found for reintroduction of the guide wire. In this case, a guide wire is introduced through the first lumen (wire lumen) extending over the entire length of the balloon dilatation catheter. The balloon dilatation catheter is therefore now guided in a conventional manner and not in accordance with the monorail system.

An important advantage of the catheter system according to the invention is that the guide wire, as in the "monorail catheter" disclosed in U.S. Pat. No. 4,762,129, can be moved substantially free of friction in accordance with the sliding rail principle.

According to one development of the invention, the shaft of the balloon dilatation catheter has, in the area of the side openings arranged proximal of the balloon, a greater external diameter than the adjacent shaft area, and the outlet opening for the guide wire is arranged in a step-shaped transition area. In this way the friction of the guide wire on the catheter shaft can be kept especially low.

According to a further advantageous embodiment, the shaft is coaxial in cross-section. In the case of a particularly rigid shaft of this type, a temporary strengthening wire may be unnecessary.

DETAILED DESCRIPTION OF THE INVENTION

Figure 1:
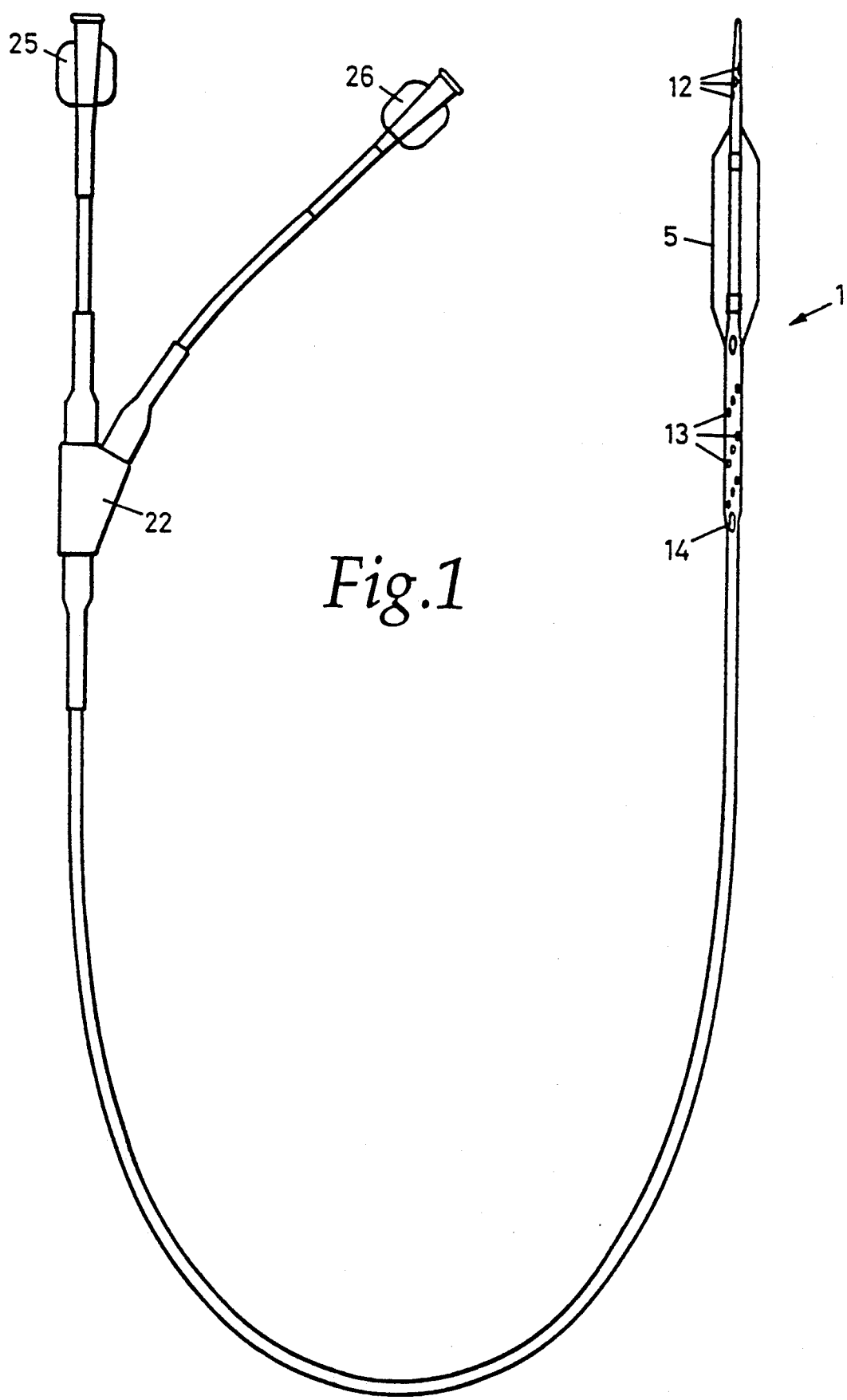
Figure 4:
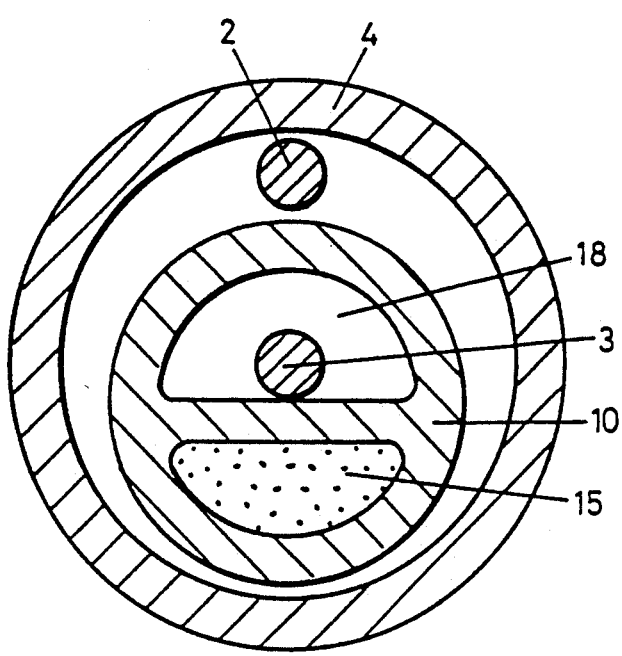
Figure 5:
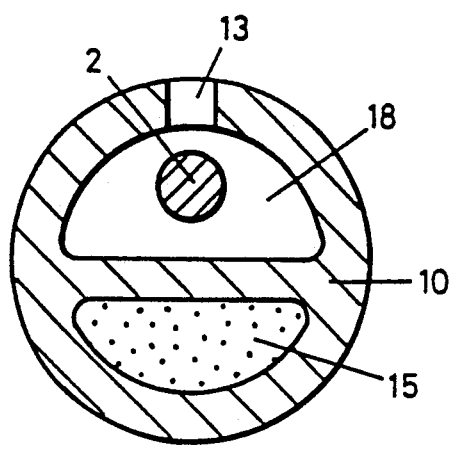
Figure 6:
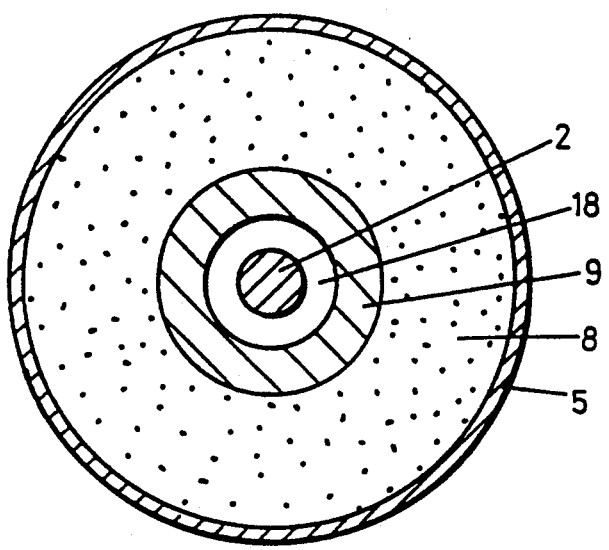
Figure 7:
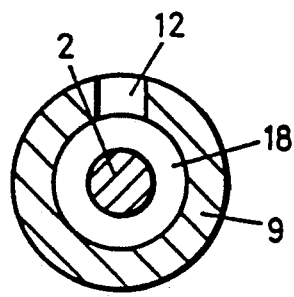
Figure 8:
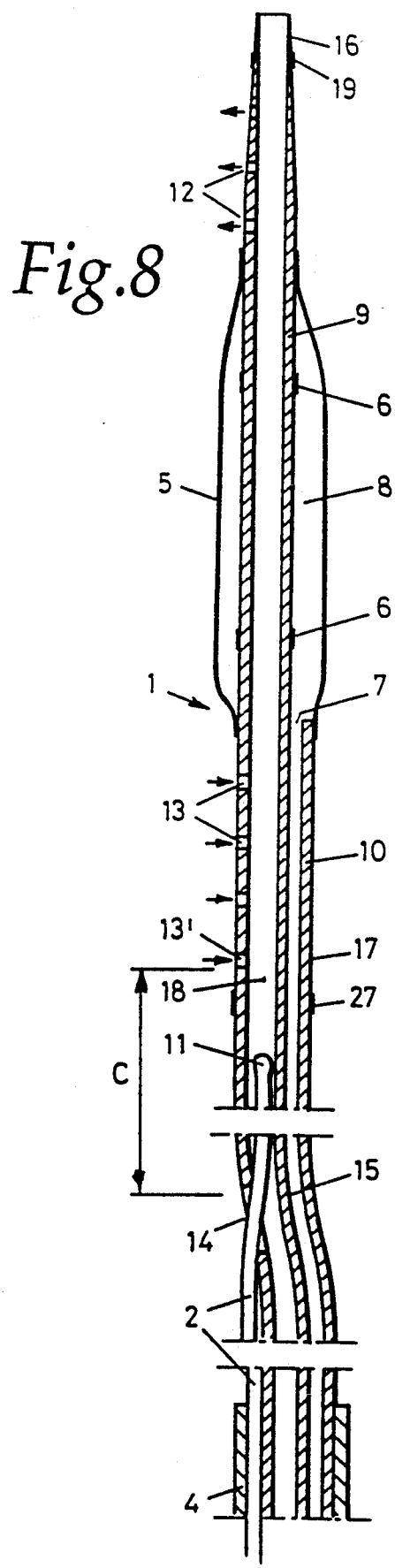
Figure 9:
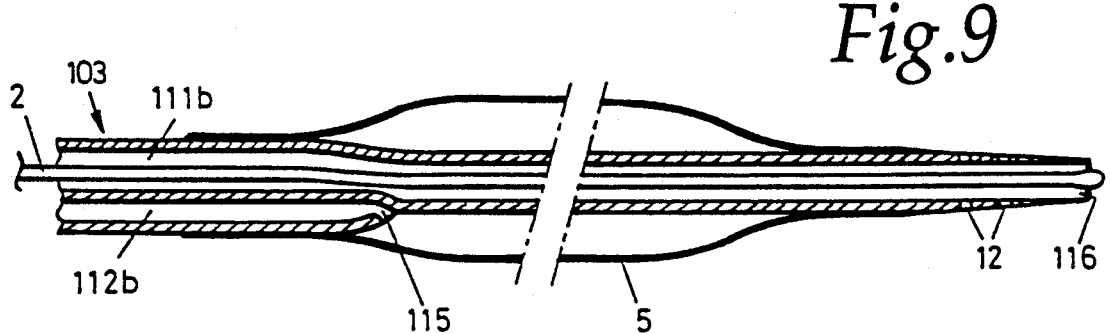
Figure 10:
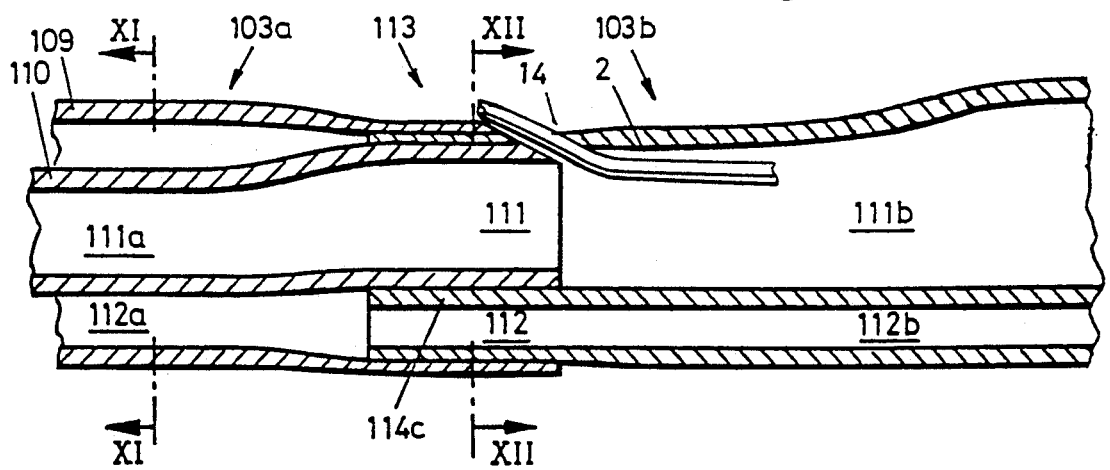
Figure 11:
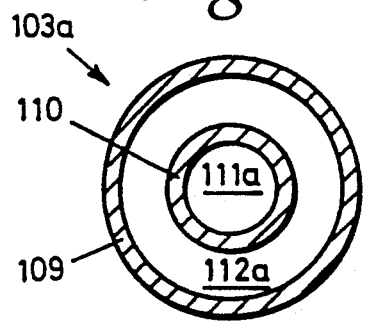
Figure 12:
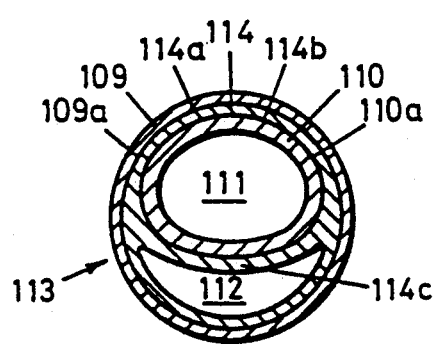

Exemplary embodiments of the invention are illustrated in greater detail with reference to the drawings, in which:

FIG. 1 shows a view of a balloon dilatation catheter,

FIG. 2 shows a cross-section through a distal area of a catheter system according to the invention, FIG. 3 shows a view of a proximal area of the catheter system according to the invention, FIG. 4 shows a cross-section along the line IV—IV in FIG. 2, FIG. 5 shows a cross-section along the line V—V in FIG. 2, FIG. 6 shows a cross-section along the line VI—VI in FIG. 2, FIG. 7 shows a cross-section along the line VII—VII in FIG. 2, FIG. 8 shows a view of a catheter system according to the invention in accordance with FIG. 2, but with the controllable guide wire drawn partially back for the purpose of unimpeded perfusion, FIG. 9 shows, in longitudinal section, the distal area of a catheter system according to the invention in one alternative, FIG. 10 shows a section through the shaft/balloon connection point of the catheter system according to the alternative, FIG. 11 shows a section along the line XI—XI in FIG. 10, and FIG. 12 shows a section along the line XII—XII in FIG. 10.

The catheter system according to the invention shown in FIGS. 1 to 7 has a balloon dilatation catheter 1, a guide catheter 4, a temporary strengthening wire 3 and a guide wire 2. As FIGS. 2 and 3 show, the strengthening wire 3, the balloon dilatation catheter 1 and the guide catheter 4 are arranged coaxial to one another. A seal (not shown here) is arranged in a connection piece 20 of the guide catheter 4 and seals off the guide catheter 4 with respect to the dilatation catheter 1. The guide wire 2 extends alongside the balloon dilatation catheter 1 and parallel to the latter in the guide catheter 4. The strengthening wire 3 is sealed displaceably in a branch 23 of a branch piece 22 of the balloon dilatation catheter 1 and terminates at its distal end in front of a lateral outlet opening 14 of the balloon dilatation catheter 1. A further branch 24 of the branch piece 22 serves for dilatation of a balloon 5 of the catheter 1 and is for this purpose connected to it via a pressure lumen 15. For the injection of contrast media or flushing solution, a lateral attachment 21 is also arranged on the connection piece 20.

The balloon 5 is connected in a known manner to a two-lumen shaft 17 of the balloon dilatation catheter 1. As FIG. 2 shows, the shaft 17 and the guide wire 2 emerge at the distal end of the insertion catheter 4. Distal and proximal of the balloon 5, the shaft 17 has in each case a number of side openings 12 and 13, respectively. These openings 12 and 13 are connected to one another via a lumen 18 of the shaft 17. These side openings permit a perfusion of blood plasma even during dilatation with a corresponding pressure difference upstream and downstream of the stenosis.

In the area of the proximal side openings 13, the external diameter of the shaft 10 is greater in an area C than before the outlet opening 14. As can be seen in FIG. 2, the outlet opening 14 is arranged at a step-like shoulder of the shaft 17. As can be seen in FIG. 1, the outlet opening 14 has the form of a longitudinal slot.

So that an unimpeded perfusion is possible for vessel fluid during dilatation of a stenosis, the controllable guide wire 2 is pulled back, as shown in FIG. 8, until its distal end 11 lies proximal of the side opening 13′ furthest removed from the end hole 16 of the dilatation catheter. By means of a gold marking 27, the appropriate position for the end 11 of the guide wire 2 can be visualised by X-ray. The distance C between the gold marking 27 and the outlet opening 14 is chosen comparatively large and amounts, for example, to 10–30 cm. This ensures that the guide wire 2, which is very narrow and extremely flexible in the distal area, can be pushed back into the balloon after its partial withdrawal.

For determining the position of the dilatation balloon, two marking rings 6 which are opaque to X-ray are arranged on the shaft 9.

The temporary strengthening wire 3 is a simple wire, which can be teflonised on the outside in order to reduce the sliding friction. Its length is for example 1.20 m. The external diameter of the shaft 17 is preferably about 1.5 mm in the area of the side openings 13 and about 1.4 mm proximal of the outlet opening 14. The shaft 17 is comparatively soft without the strengthening wire 3.

For dilatation of a stenosis, the guide catheter 4 is advanced percutaneously as far as the stenosis, for example via an artery of the leg. The guide wire 2 is then advanced through the guide catheter 4 until its distal end lies distal of the stenosis. The important point is that, because of the low friction of the guide wire, the latter can be controlled freely and virtually unimpeded. Once the guide wire 2 with its distal end is lying in the stenosis, the balloon dilatation catheter 1 is pushed onto the guide wire 2 and is advanced by sliding along the latter until the balloon 5 is lying in the stenosis. The balloon 5 is then dilated in a known manner by means of the pressure fluid 8. On displacement of the balloon dilatation catheter and also in the case of catheter replacement, the guide wire 2 is fixed at its proximal end. Since, as has been mentioned above, there is a perfusion of blood plasma through the side openings 12 and 13 even during dilatation, it is possible for dilatation to be carried out for a longer period of time using the catheter system according to the invention. Should the perfusion be obstructed by blood which has coagulated at the openings 12 and 13, these openings can be flushed with, for example, a heparin solution via the lumen 18.

So that perfusion is not impeded by the guide wire 2 during dilatation, the guide wire 2 is withdrawn completely or partially from the balloon segment. Once the guide wire has left the lateral outlet opening, it can no longer be introduced into the balloon segment. The guide wire 2 is therefore introduced into the second lumen 18 via the branch piece 23 or 25.

In a preferred treatment procedure, the stenosis is dilated in a first step using a catheter according to the "monorail system". After removal of the "monorail" balloon dilatation catheter, the balloon dilatation catheter 1 is pushed onto the already indwelling guide wire 2, the guide wire leaving the catheter 1 through the outlet opening 14, and the catheter 1 thus being displaceable in accordance with the sliding rail principle. For its insertion, the catheter 1 can be provided with the temporary strengthening wire 3. Prior to the dilatation of the stenosis with the catheter 1, the guide wire 2 is withdrawn in order to improve the perfusion. A new guide wire 2 is introduced via the branch piece 23 or 25 whenever such a guide wire should prove necessary for the subsequent procedure.

FIGS. 9 to 12 show a design of the catheter system according to the invention, which differs from the abovementioned design particularly in that a shaft 103 is provided which is coaxial in cross-section and comparatively stiff. The advantage of this is that a temporary strengthening wire may be omitted.

The guide wire 2 is displaceable in the longitudinal direction in a continuous first lumen 111 of the dilatation catheter. The interior of the balloon 5 is connected via a second lumen 112 to a pressure-suction device (not shown here).

The flexible shaft 103 is connected at its distal end to the balloon 5. FIG. 9 shows the balloon 5, which is connected via an opening 115 to the second lumen 112. By means of the said pressure-suction device, the balloon 5 can be folded for its insertion into the vessel and can be dilated for treatment of a stenosis. As shown in FIG. 9, the guide wire 2 can be advanced at its distal end through an opening 116 right through the dilatation balloon 5. It is, as is known, particularly flexible and yet torsionally strong at its distal end.

The shaft 103 is produced from a proximal portion 103a and a distal portion 103b. These portions 103a and 103b are produced separately and are connected to one another at the connection point 113. As FIGS. 11 and 12 show, the cross-sections of the two portions 103a and 103b are different. The proximal portion 103a consists of two coaxial tube pieces 109 and 110, the inner tube piece 110 forming a lumen 111a for the guide wire 2. The space between the tube pieces 109 and 110 forms a lumen 112a, in which pressure fluid can circulate between the balloon 5 and the pressure-suction pump. The tube pieces 109 and 110 have a circular cross-section and consist of a thermoplastic material.

The shaft portion 103b consists of a two-lumen, extruded tube piece, which is connected in a known manner to the balloon 5. A first approximately circular lumen 111b serves for receiving the guide wire 2, and a second crescent-shaped lumen 112b serves for receiving the pressure fluid. Both lumina are separated from each other by a separating wall 114c formed on the portion 103b.

According to FIG. 10, the portions 103a and 103b are connected to one another in such a way that the lumina 111a and 111b form the first lumen 111 and the lumina 112a and 112b form the lumen 112. The lumina 111 and 112 are thus also separated completely from one another at the connection point 113. In order to connect the separately produced portions 103a and 103b to one another, they are pushed together until the corresponding ends overlap by a length of several millimeters.

The two tube portions 103a and 103b are preferably welded to one another in the area of the connection point 113. The outer surface 114a of the tube piece 114 is preferably welded to the inner surface 109a of the tube piece 109, and the outer side 110a of the tube piece 110 is preferably welded to the inner side 114b of the tube piece 114. A design is also possible in which the tube piece 114 has a reduced wall thickness at the end to be connected. This reduced wall thickness can in this case also be obtained, for example, by grinding down the outer side 114a of the tube piece 114. A design is also conceivable in which the two portions 103a and 103b are glued to one another in the overlapping area 113.

If the portions 103a and 103b are made of identical or similar plastic and if the wall thicknesses are approximately equal, the tube piece 103a has a greater rigidity than the tube piece 103b. The principle reason for the different rigidity lies in the fact that the tube piece 103a in the longitudinal section according to FIG. 10 consists of four wall areas, and the portion 103b consists of only three wall areas. The different rigidity is thus primarily due to the different structures of the two portions 103a and 103b.

The length of the more flexible portion 103b is preferably adapted to the length of the curved portion of the blood vessel to be treated.

In the rigid but essentially straight portion 103a, the guide wire 2 slides especially easily because the lumen 111a is essentially circular. This can be improved still further by means of suitable coatings of the guide wire 2 and of the inner side of the tube piece 110.

The design according to FIGS. 9 to 12 has the advantage that it is comparatively hard and thus less susceptible to buckling upon insertion. The shaft also has a thinner wall, as a result of which the balloon can be filled and emptied more quickly, which is of course very important in surgical treatment.

The outlet opening 14 for the guide wire 2 is preferably arranged in the overlapping area of the two shaft portions 103a and 103b, as shown in FIG. 10. A comparatively level path of the guide wire 2 is achieved by means of the adjoining shoulder of the shaft distal of the overlapping area.

The catheter system according to the invention is particularly suitable as a so-called "emergency catheter", in other words when, after a dissection, a comparatively long-term dilatation is required.

We claim:

1. A balloon dilatation perfusion catheter, comprising:
    a balloon defining a balloon cavity therein;
    a bilumen tubular member having a proximal end and a distal end extending through the balloon cavity;
    a plurality of side openings arranged in the bilumen tubular member located both distal and proximal of the balloon and in fluid communication with one another via a first lumen in the bilumen tubular member, the first lumen extending from the proximal end of the bilumen tubular member through the tubular member to an end hole distal of the balloon;
    a guide wire outlet opening in the bilumen tubular member proximal of the balloon in communication with the first lumen; and
    a second lumen in the bilumen tubular member extending from the proximal end of the bilumen tubular member to the balloon and in fluid communication with the balloon cavity wherein the first lumen is provided for receiving a guide wire or a temporary strengthening wire therein and for flushing the side openings with a liquid, and the second lumen is provided for receiving a pressure fluid for inflating the balloon.

2. A balloon dilatation perfusion catheter of claim 1 wherein the bilumen tubular member in the area of the side openings proximal of the balloon has a greater external diameter than a proximally adjoining bilumen tubular member area, and wherein the guide wire outlet opening is arranged in a step-like transition area.

3. A balloon dilatation perfusion catheter of claim 2 wherein the guide wire outlet has the form of a longitudinal slot.

4. A balloon dilatation perfusion catheter of claim 2 wherein the distance (C) between the guide wire outlet opening and the nearest side opening proximal of the balloon is such that, after partial withdrawal of the guide wire from the first lumen until its distal tip lies proximal of the nearest side opening, the guide wire can again be advanced distally.

5. A balloon dilatation perfusion catheter of claim 4 wherein the distance (C) is from 10 to 30 cm.

6. A balloon dilatation perfusion catheter of claim 1 wherein the guide wire outlet opening has the form of a longitudinal slot.

7. A balloon dilatation perfusion catheter of claim 6 wherein the distance (C) between the guide wire outlet opening and the nearest side opening proximal of the balloon is such that, after partial withdrawal of the guide wire from the first lumen until its distal tip lies proximal of the nearest side opening, the guide wire can again be advanced distally.

8. A balloon dilatation perfusion catheter of claim 7 wherein the distance (C) is from 10 to 30 cm.

9. A balloon dilatation perfusion catheter of claim 1 wherein the bilumen tubular member is marked with a color in the area of the guide wire outlet opening.

10. A balloon dilatation perfusion catheter according to claim 1 wherein the distance (C) between the guide wire outlet opening and the nearest side opening proximal of the balloon is such that, after partial withdrawal of the guide wire from the first lumen until its distal tip lies proximal of the nearest side opening, the guide wire can again be advanced distally.

11. A balloon dilatation perfusion catheter of claim 10 wherein the distance (C) is from 10 to 30 cm.

12. A balloon dilatation perfusion catheter of claim 11 wherein the balloon dilatation catheter has an X-ray opaque marking for determining the appropriate position of the distal tip of the guide wire upon the partial withdrawal thereof.

13. A balloon dilatation perfusion catheter, comprising:
   a balloon defining a balloon cavity;
   a distal shaft having a proximal portion and a distal portion with the distal portion defining a single lumen tube with a first lumen extending through the balloon cavity to an end hole distal of the balloon and the proximal portion defining a bilumen tube with a second lumen in fluid communication with the first lumen and a third lumen, with the distal shaft further having side openings arranged both distal and proximal of the balloon and in fluid communication with one another via the first lumen and the second lumen;
   a proximal outer shaft having a proximal end and a distal end;
   a proximal inner shaft having a proximal end and a distal end with the proximal inner shaft defining a fourth lumen therethrough, the proximal inner shaft being coaxially disposed in the proximal outer shaft to define a fifth lumen in an annular space formed between the proximal inner shaft and the proximal outer shaft wherein the distal end of the proximal inner shaft and the distal end of the proximal outer shaft are connected to the proximal portion of the distal shaft in such a way that the second lumen of the distal shaft is connected to the fourth lumen of the proximal inner shaft and the third lumen of the distal shaft is connected to the fifth lumen of the proximal outer shaft; and
   a guide wire outlet opening in communication with the second lumen of the distal shaft located adjacent to the proximal portion of the distal shaft.

14. A balloon dilatation perfusion catheter of claim 13 wherein the distal end of the proximal outer shaft and the distal end of the proximal inner shaft overlap with the proximal end of the distal shaft and are welded together at the adjoining surfaces.

15. A balloon dilatation perfusion catheter of claim 14 wherein at least one of the proximal outer shaft and distal shaft has a reduced wall thickness at the end connected to the other portion.

16. A balloon dilatation perfusion catheter of claim 13 wherein at least one of the proximal outer shaft and distal shaft has a reduced wall thickness at the end connected to the other portion.

* * * * *